US00PP33191P2

(12) United States Plant Patent
Van Dijk

(10) Patent No.: US PP33,191 P2
(45) Date of Patent: Jun. 22, 2021

(54) ***ANTHURIUM* PLANT NAMED 'ANTHIJTDEN'**

(50) Latin Name: ***Anthurium andraeanum* L.**
Varietal Denomination: ANTHIJTDEN

(71) Applicant: ANTHURA B.V., Bleiswijk (NL)

(72) Inventor: Jan Van Dijk, Bleiswijk (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 16/974,222

(22) Filed: Nov. 18, 2020

(51) Int. Cl.
*A01H 5/02* (2018.01)
*A01H 6/10* (2018.01)

(52) U.S. Cl.
USPC ..... Plt./365

(58) Field of Classification Search
USPC ..... Plt./365
See application file for complete search history.

*Primary Examiner* — Susan McCormick Ewoldt
(74) *Attorney, Agent, or Firm* — Jondle & Associates, P.C.

(57) ABSTRACT

A new *Anthurium* cut flower plant named 'ANTHIJTDEN' particularly distinguished by having shiny and strongly blistered, red, orbicular-cordate, and durable spathes that retain the original color for a very long period of time, shiny, dark green, and elliptical-cordate, durable leaves, white spadices with yellow-green tips, early and rich flowering continuously throughout the year, and a plant height of 60.0 cm to 70.0 cm is disclosed.

3 Drawing Sheets

Genus and species: *Anthurium andraeanum* L.
Variety denomination: 'ANTHIJTDEN'.

BACKGROUND OF THE NEW PLANT

The present invention comprises a new and distinct variety of *Anthurium*, botanically known as *Anthurium andraeanum* L., and hereinafter referred to by the variety name 'ANTHIJTDEN'. The new *Anthurium* plant is a product of a planned breeding program conducted by the inventor in Bleiswijk, the Netherlands. The objective of this breeding program was to create a new cut flower plant with a height of 60.0 cm to 70.0 cm having strongly blistered, shiny, red, orbicular-cordate, and durable spathes.

The new variety originated from a cross-pollination made in June 2006 in Bleiswijk, the Netherlands. The female parent was a red *Anthurium* pot plant designated '7658-03' (unpatented), and the male parent was a red *Anthurium* pot plant designated '8138-02' (unpatented).

A single plant was selected from the progeny of the stated cross in May 2009. Asexual reproduction of the new variety by tissue culture in 2016 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on May 14, 2019 (Application no. 2019/1210), by Applicant who obtained the subject matter disclosed directly from the inventor. 'ANTHIJTDEN' has not been made publicly available or sold anywhere in the world prior to the effective filing date of this application with the exception of sales or disclosures made one year or less before the effective filing date of this claimed invention by Applicant who obtained 'ANTHIJTDEN' directly from the inventor.

SUMMARY OF THE INVENTION

The following are the most outstanding and distinguishing characteristics of this new variety when grown under normal horticultural practices in Bleiswijk, the Netherlands:

1) Strongly blistered, shiny, red, orbicular-cordate spathes;
2) White spadices with yellow-green tips;
3) Shiny, dark green, elliptical-cordate leaves; and
4) Relative position of spathe lobes is adpressed.

DESCRIPTION OF THE PHOTOGRAPHS

This new *Anthurium* plant is illustrated by the accompanying photographs which show the overall plant habit including blooms, bud, and foliage of the plant; the colors shown are as true as can be reasonably obtained by conventional photographic procedures. The photographs are of a 60-week-old plant grown in a greenhouse in Bleiswijk, the Netherlands, in October 2020. Colors in the photographs may differ from the color values cited in the detailed botanical description, which accurately describe the actual colors of the new variety.

DESCRIPTION OF THE NEW VARIETY

Figure 1:
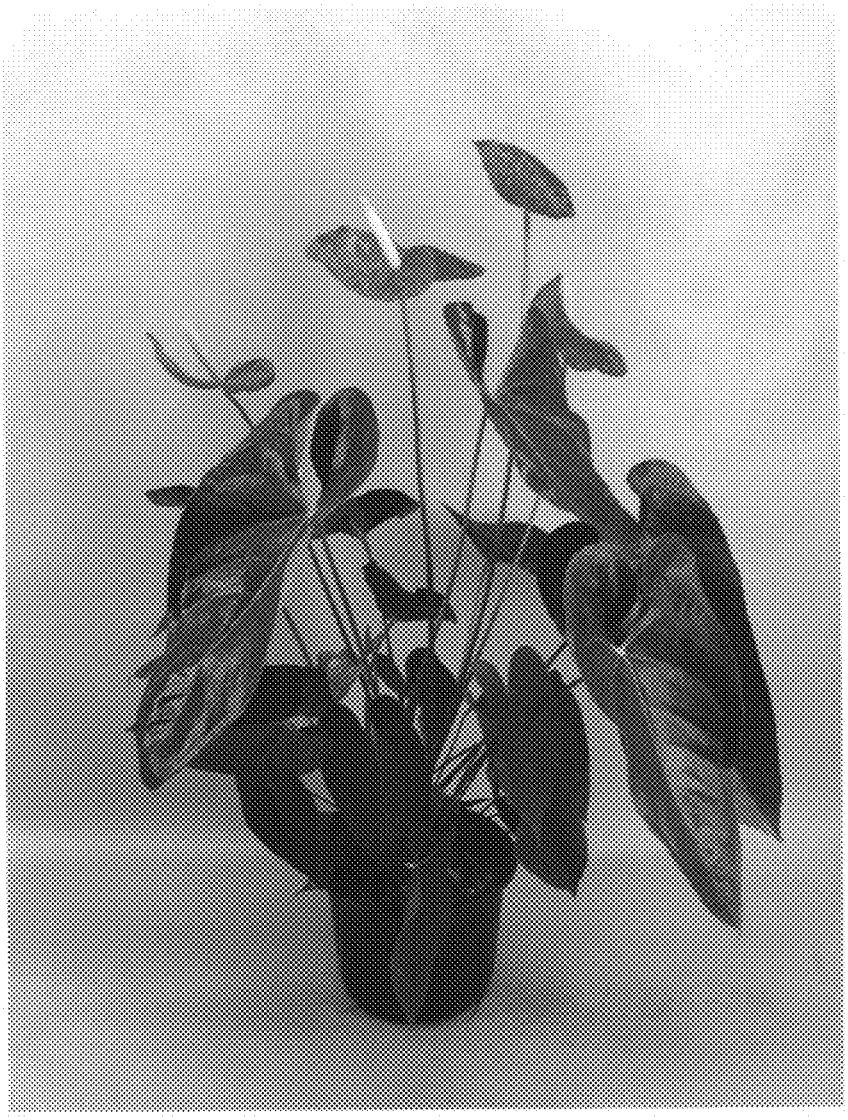
FIG. 1 shows the overall plant habit, including blooms, bud, and foliage.
Figure 2:
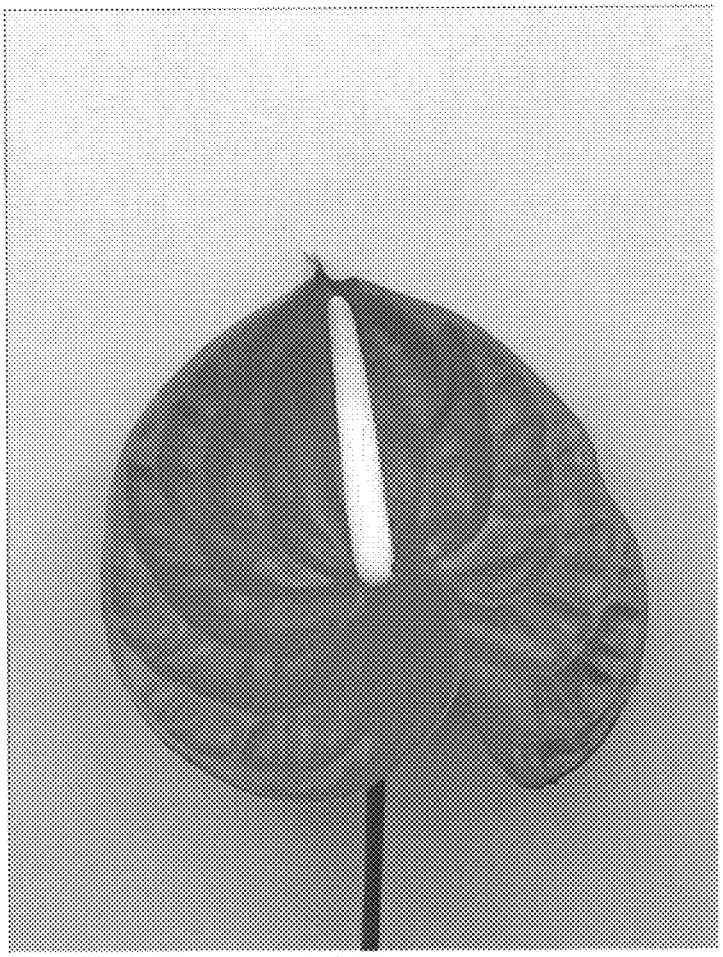
FIG. 2 shows a close-up of the mature spathe.
Figure 3:
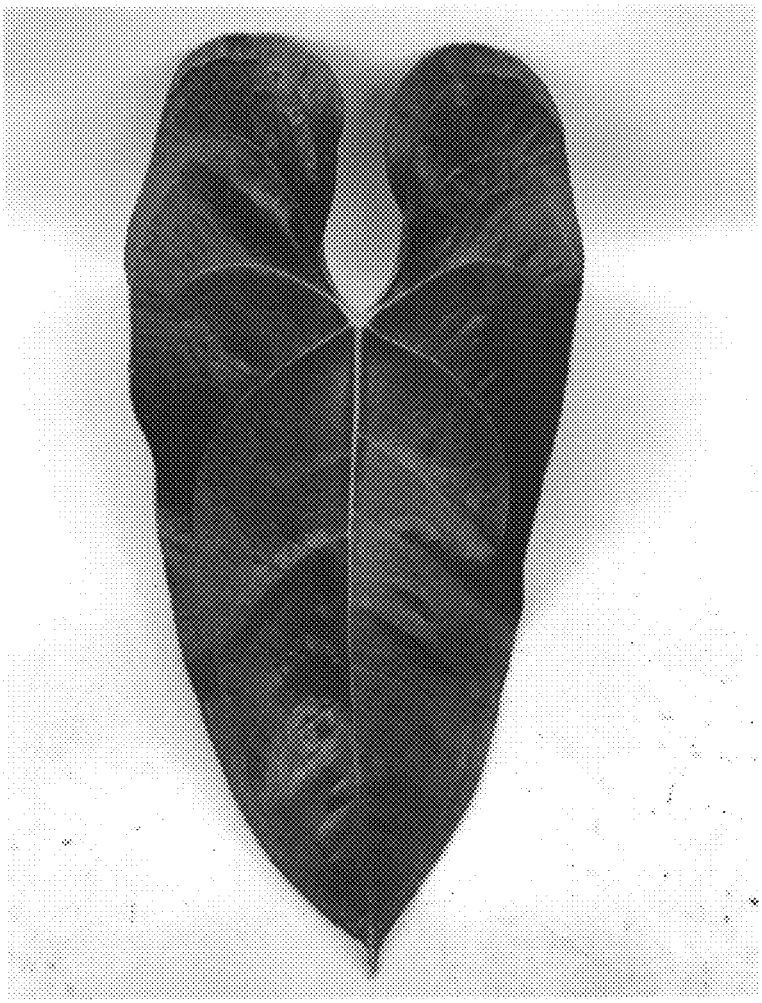
FIG. 3 shows a close-up of the upper leaf blade surface.

The following detailed description sets forth the distinctive characteristics of 'ANTHIJTDEN'. The data which define these characteristics were collected from asexual reproductions carried out in Bleiswijk, the Netherlands. The plant history was taken on 60-week-old plants which were planted from tissue culture in 7-centimeter (diameter) pots and grown in a glass greenhouse between 19° C. and 24° C. Observations were made in October 2020. Color readings were taken under 5000 lux natural light in the greenhouse. Color references are primarily to The R.H.S. Colour Chart of The Royal Horticultural Society of London (R.H.S.) (2015).

DETAILED BOTANICAL DESCRIPTION

Classification:
*Family*.—Araceae.
*Botanical*.—*Anthurium andraeanum* L.

*Common name.*—*Anthurium.*

*Denomination.*—'ANTHIJTDEN'.

Parentage:

*Female parent.*—*Anthurium* plant '7658-03' (unpatented).

*Male parent.*—*Anthurium* plant '8138-02' (unpatented).

Plant:

*Propagation.*—Tissue culture.

*Root description.*—Fleshy-creamy (RHS 158A) colored roots with small hairy lateral roots having yellow (RHS 7A) colored root tips.

*Time to produce a finished flowering plant.*—55 to 66 weeks after planting in a 17-cm (diameter) pot.

*Growth habit.*—Upright.

*Height* (*measured from soil, including inflorescence*).—60.0 cm to 70.0 cm.

*Width* (*measured from leaf tips*).—53.0 cm to 58.0 cm.

Leaves:

*Immature leaves.*—Length: 25.0 cm to 30.0 cm. Width: 14.0 cm to 17.0 cm. Color: Upper surface: RHS 146A. Lower surface: RHS 146B. Texture (both upper and lower surfaces): Leathery, soft, thin, and glossy.

*Mature leaves.*—Length (fully expanded): 31.0 cm to 36.0 cm. Width: 18.0 cm to 20.0 cm. Shape: Elliptical cordate. Apex: Acuminate. Base: Cordate. Leaf blade angle with the petiole: Between 90 degrees and 110 degrees. Leaf margin: Entire Color: Upper surface: RHS 147A. Lower surface: RHS 146B. Texture (both upper and lower surfaces): Leathery, thick, smooth, and glossy. Venation: Pinnate veining; the mid-vein and primary veins (the veins that radiate out from the junction of petiole and leaf) protrude at the underside of the leaf blade. Venation color: Upper surface: RHS 146B Lower surface: RHS 146C

*Lobes.*—Present. Arrangement: Leaf blade has two lobes extending past the petiole. The lobes are non-touching. Length of lobes of mature leaf blades: 8.0 cm to 9.0 cm. Width of lobes of mature leaf blades: 7.0 cm to 8.0 cm. Distance from petiole/leaf junction to highest point on lobes of mature leaf blades: 4.0 cm to 5.0 cm.

*Petiole.*—Cross-section: Round. Diameter: 0.4 cm to 0.5 cm. Length: 34.0 cm to 39.0 cm for a mature leaf size. Color: Mature leaf: RHS 144B. Immature leaf: RHS 144C. Cataphyll color surrounding the petiole: Outside: RHS 144B. Inside: RHS 145C.

*Geniculum.*—Length: 1.5 cm to 2.0 cm. Width: 0.5 cm to 0.6 cm. Color: RHS 144B.

Inflorescence:

*Arrangement.*—Single.

*Flowering habit* (*length of flowering season*).—Continuous.

*Number of inflorescences per plant.*—The plant produces 4 to 6 flowers in the period of one year.

*Fragrance.*—Absent.

*Longevity of inflorescence as a cut flower.*—30 to 35 days.

Spathe:

*Buds.*—The spathe is tightly rolled around the spadix and extrudes from the peduncle sheath.

*Arrangement.*—Spathe angle with the peduncle is between 130 degrees and 140 degrees; the spathe stands on a wiry peduncle about 7.0 cm to 10.0 cm above the foliage.

*Shape.*—Orbicular cordate.

*Apex.*—Mucronate.

*Base.*—Cordate.

*Texture.*—Strongly blistered and shiny.

*Margin.*—Undulated.

*Size.*—Length: 15.0 cm to 16.0 cm. Width: 13.5 cm to 14.5 cm.

*Lobes.*—Present. Arrangement: The spathe has two lobes extending past the peduncle. The lobes are adpressed. Length: 5.0 cm to 6.0 cm. Width: 7.5 cm to 8.5 cm.

*Color.*—Just fully open: Upper surface: RHS 45A. Lower surface: RHS 45B. This red color remains for a very long period, at least more than 30 weeks after opening.

Peduncle:

*Shape.*—Erect.

*Cross-section.*—Round.

*Length.*—53.0 cm to 58.0 cm.

*Diameter.*—0.4 cm to 0.5 cm.

*Color.*—At the base RHS 144B; becomes red (RHS 180B) toward the spathe.

Flowering time:

*General.*—One small, rooted, untreated tissue culture plant of 4.0 cm tall will flower for the first time, depending on the season, after 30 to 35 weeks.

Spadix:

*Size.*—Length: 7.0 cm to 7.5 cm (depending on flower size). Width (at apex): 0.6 cm to 0.8 cm. Width (at base): 0.8 cm to 1.0 cm.

*Shape.*—Columnar.

*Angle of spadix tip with peduncle.*—160 degrees to 170 degrees.

*Texture.*—When the spathe is unfurling the spadix is smooth. When the spadix matures, small stigmata protrude. The stigmata are evenly distributed around the spadix. The spadix matures from base to top, slowly giving the spadix a somewhat rough appearance.

*Color.*—Immature: RHS 15A and RHS 151A toward the tip. Mature: RHS 158D. Ages to: RHS 153D.

Flowers:

*Quantity per spadix.*—270 to 350.

*Spadix flower arrangement.*—Bisexual, rounded in cross-section.

*Shape.*—Rounded.

*Size.*—Length: 0.05 cm to 0.10 cm. Diameter (maximum): 0.10 cm.

*Color.*—RHS 156D.

Reproductive organs:

*Stamens.*—Not visible.

*Pollen amount.*—Absent.

*Pistil.*—Quantity: 270 to 350. Length: Less than 0.01 cm. Color: RHS 156D.

*Style.*—Not observed to date.

*Stigma.*—Shape: Ovoid. Diameter: Less than 0.01 cm. Color: RHS 156D.

*Ovary.*—Rarely visible.

*Ovary color.*—Not measured.

Fruit and seed set: None observed to date.

Disease and pest resistance: No specific resistance or susceptibility observed to pathogens or pests common to *Anthurium* under commercial conditions to date.

COMPARISON WITH PARENTAL AND SIMILAR COMMERCIAL VARIETIES

'ANTHIJTDEN' differs from the female parent plant '7658-03' (unpatented) in that 'ANTHIJTDEN' has strongly blistered, orbicular-cordate spathes and green cataphylls, whereas '7658-03' has blistered, oblong spathes and red cataphylls.

'ANTHIJTDEN' differs from the male parent plant '8138-02' (unpatented) in that 'ANTHIJTDEN' has strongly blistered, orbicular-cordate spathes with mucronate apexes, whereas '8138-02' has weakly blistered, cordate spathes with acuminate apexes.

'ANTHIJTDEN' differs from similar commercial variety 'ANTHARES' (also known as 'Carisma'; unpatented) in that 'ANTHIJTDEN' has orbicular-cordate spathes and spathe lobes with an adpressed relative position, whereas 'ANTHARES' has cordate spathes and spathe lobes with an overlapping relative position.

'ANTHIJTDEN' differs from similar variety 'TROPICAL' (unpatented) in that 'ANTHIJTDEN' has orbicular-cordate spathes and green cataphylls, whereas 'TROPICAL' has oblong spathes and red cataphylls.

I claim:

1. A new and distinct variety of *Anthurium* plant named 'ANTHIJTDEN', substantially as illustrated and described herein.

* * * * *